US012688925B2

(12) United States Patent
Chen et al.

(10) Patent No.: US 12,688,925 B2
(45) Date of Patent: Jul. 21, 2026

(54) METHOD AND DEVICE FOR PRESENTING FOOD INFORMATION AND COMPUTER READABLE STORAGE MEDIUM

(71) Applicant: Wistron Corporation, New Taipei City (TW)

(72) Inventors: Wei Ying Chen, New Taipei City (TW); I Hua Wang, New Taipei City (TW)

(73) Assignee: Wistron Corporation, New Taipei City (TW)

( * ) Notice: Subject to any disclaimer, the term of this patent is extended or adjusted under 35 U.S.C. 154(b) by 549 days.

(21) Appl. No.: 18/297,651

(22) Filed: Apr. 10, 2023

(65) Prior Publication Data

US 2024/0177825 A1 May 30, 2024

Related U.S. Application Data

(60) Provisional application No. 63/428,418, filed on Nov. 29, 2022.

(30) Foreign Application Priority Data

Feb. 21, 2023 (TW) ................................. 112106263

(51) Int. Cl.
*G16H 20/60* (2018.01)
*G06T 11/26* (2026.01)
(52) U.S. Cl.
CPC ............. *G16H 20/60* (2018.01); *G06T 11/26* (2026.01)

(58) Field of Classification Search
CPC .............................. G16H 20/60; G06T 11/206
See application file for complete search history.

(56) References Cited

U.S. PATENT DOCUMENTS

| | | | | |
|---|---|---|---|---|
| 4,951,197 A * | 8/1990 | Mellinger | .............. | G16H 20/30 |
| | | | | 600/587 |
| 5,454,721 A * | 10/1995 | Kuch | ................. | G09B 19/0092 |
| | | | | 434/428 |
| 11,138,901 B1 * | 10/2021 | Angel | .................... | G06V 20/00 |
| 11,562,817 B2 * | 1/2023 | Kim | ....................... | G06V 10/25 |
| 11,568,760 B1 * | 1/2023 | Meier | .................. | G06V 10/764 |
| 12,394,205 B1 * | 8/2025 | Gong | .................... | G06V 20/52 |
| 2011/0077471 A1 * | 3/2011 | King | .................... | A61B 5/7445 |
| | | | | 600/300 |

(Continued)

FOREIGN PATENT DOCUMENTS

| | | |
|---|---|---|
| CN | 105022908 | 11/2015 |
| CN | 107463894 | 12/2017 |
| TW | 201228632 | 7/2012 |

*Primary Examiner* — Malina D. Blaise
(74) *Attorney, Agent, or Firm* — JCIPRNET

(57) ABSTRACT

A method and device for presenting food information and a computer readable storage medium are provided. The method includes: obtaining a recommended calorie intake of a user; determining a reference portion size of each of multiple food types based on the recommended calorie intake; determining a relative portion size of the reference portion size of each of the food types relative to a reference object; determining a food volume corresponding to the relative portion size of each of the food types according to an object volume of the reference object; and generating a pie chart according to the food volume corresponding to each of the food types.

18 Claims, 6 Drawing Sheets

(56) References Cited

U.S. PATENT DOCUMENTS

| | | | | |
|---|---|---|---|---|
| 2011/0281245 | A1* | 11/2011 | Mansour | G09B 19/0092 |
| | | | | 434/127 |
| 2012/0144912 | A1* | 6/2012 | Kates | G01F 13/008 |
| | | | | 73/149 |
| 2012/0179665 | A1* | 7/2012 | Baarman | G16H 20/60 |
| | | | | 707/E17.014 |
| 2014/0349256 | A1* | 11/2014 | Connor | A47G 21/02 |
| | | | | 434/127 |
| 2016/0166195 | A1* | 6/2016 | Radecka | A61B 5/112 |
| | | | | 600/595 |
| 2019/0313684 | A1* | 10/2019 | Wilson | G16H 20/10 |
| 2020/0043596 | A1* | 2/2020 | Koretoff | G16H 50/30 |
| 2020/0053262 | A1* | 2/2020 | Wexler | G06V 20/30 |
| 2022/0254175 | A1* | 8/2022 | Heinrich | G06V 40/117 |
| 2022/0319665 | A1* | 10/2022 | Wang | G16H 40/63 |
| 2023/0128193 | A1* | 4/2023 | Williams | A61B 5/7455 |
| | | | | 715/711 |

* cited by examiner

METHOD AND DEVICE FOR PRESENTING FOOD INFORMATION AND COMPUTER READABLE STORAGE MEDIUM

CROSS-REFERENCE TO RELATED APPLICATION

This application claims the priority benefit of U.S. provisional application Ser. No. 63/428,418, filed on Nov. 29, 2022, and Taiwan application serial no. 112106263, filed on Feb. 21, 2023. The entirety of each of the above-mentioned patent applications is hereby incorporated by reference herein and made a part of this specification.

BACKGROUND

Technical Field

The disclosure relates to an information presentation technology, and in particular to a method and device for presenting food information and a computer readable storage medium.

Description of Related Art

In the prior art, although there are devices, equipment, or application programs for the user to record the daily dietary status, most of the relevant recording functions can only record the number of servings of the intake of each meal or separately calculate the calorie intake for each food. However, such conventional recording functions make it difficult for the user to perform a comprehensive assessment of the intake status of various food types in the diet. In addition, there is no product on the market that provides a personalized balanced recommended dietary intake calculated from personal physiological data.

SUMMARY

The disclosure provides a method and device for presenting food information and a computer readable storage medium, which can be used to solve the above technical issues.

An embodiment of the disclosure provides a method for presenting food information, which is suitable for a device for presenting food information and includes the following steps. A recommended calorie intake of a user is obtained. A reference portion size of each of multiple food types is determined based on the recommended calorie intake. A relative portion size of the reference portion size of each of the food types relative to a reference object is determined. A food volume corresponding to the relative portion size of each of the food types is determined according to an object volume of the reference object. A pie chart is generated according to the food volume corresponding to each of the food types.

An embodiment of the disclosure provides a device for presenting food information, which includes a storage circuit and a processor. The storage circuit stores a program code. The processor is coupled to the storage circuit and accesses the program code to execute the following. A recommended calorie intake of a user is obtained. A reference portion size of each of multiple food types is determined based on the recommended calorie intake. A relative portion size of the reference portion size of each of the food types relative to a reference object is determined. A food volume corresponding to the relative portion size of each of the food types is determined according to an object volume of the reference object. A pie chart is generated according to the food volume corresponding to each of the food types.

An embodiment of the disclosure provides a computer readable storage medium. The computer readable storage medium records an executable computer program. The executable computer program is loaded by a device for presenting food information to execute the following. A recommended calorie intake of a user is obtained. A reference portion size of each of multiple food types is determined based on the recommended calorie intake. A relative portion size of the reference portion size of each of the food types relative to a reference object is determined. A food volume corresponding to the relative portion size of each of the food types is determined according to an object volume of the reference object. A pie chart is generated according to the food volume corresponding to each of the food types.

DETAILED DESCRIPTION OF DISCLOSED EMBODIMENTS

Figure 1:
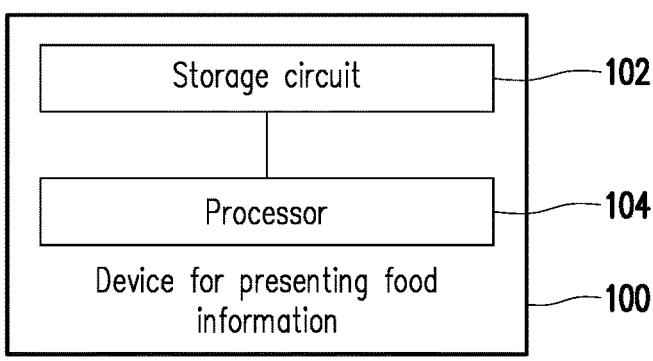
FIG. 1 is a schematic diagram of a device for presenting food information according to an embodiment of the disclosure.

Please refer to FIG. 1, which is a schematic diagram of a device for presenting food information according to an embodiment of the disclosure. In different embodiments, a device for presenting food information 100 may be, for example, implemented as various smart devices and/or computer devices, but not limited thereto.

In FIG. 1, the device for presenting food information 100 includes a storage circuit 102 and a processor 104.

The storage circuit 102 is, for example, any type of fixed or removable random access memory (RAM), read-only memory (ROM), flash memory, hard disk drive, other similar device, or a combination of the devices and may be used to record multiple program codes or modules.

The processor 104 is coupled to the storage circuit 102 and may be a general purpose processor, a specific purpose processor, a traditional processor, a digital signal processor, multiple microprocessors, one or more microprocessors combined with a digital signal processor core, a controller, a microcontroller, an application specific integrated circuit (ASIC), a field programmable gate array (FPGA), any other types of integrated circuits, state machines, advanced RISC machine (ARM)-based processors, and the like.

In the embodiment of the disclosure, the processor 104 may access the modules and the program codes recorded in the storage circuit 102 to implement a method for presenting food information proposed by the disclosure, and the details thereof are described below.

Figure 2:
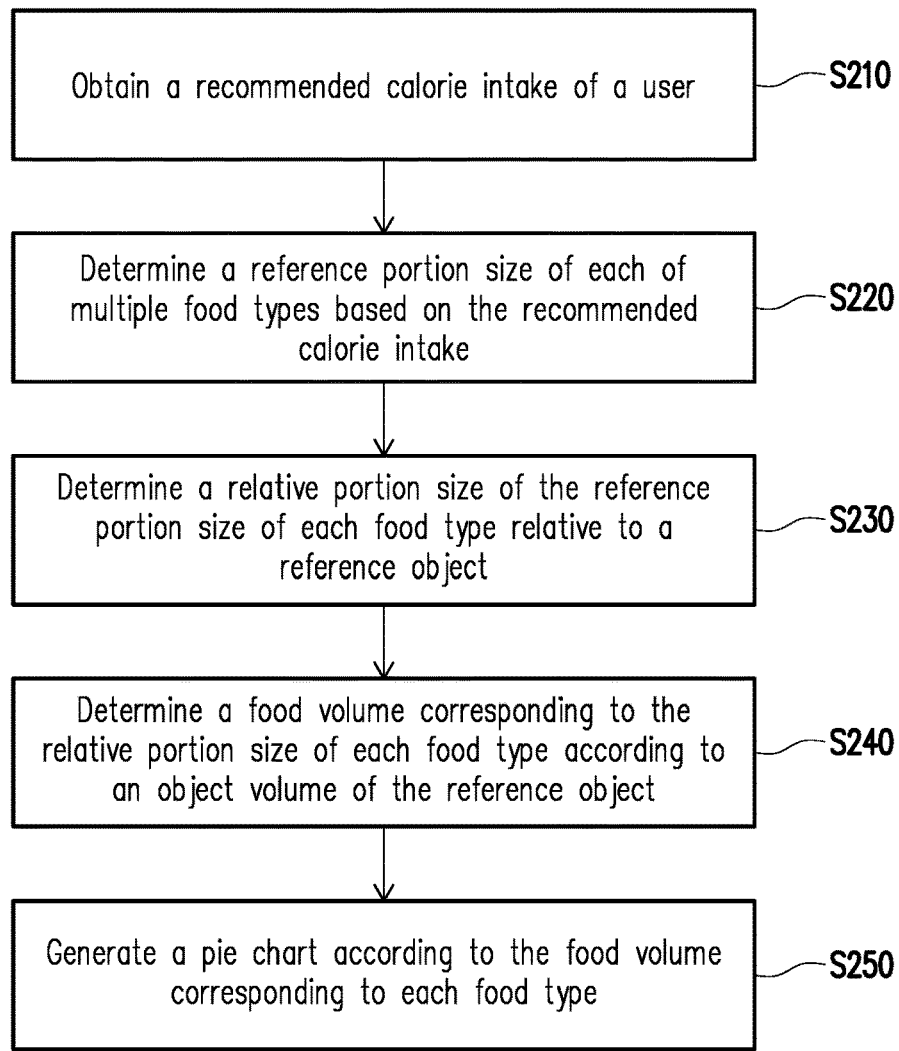
FIG. 2 is a flowchart of a method for presenting food information according to an embodiment of the disclosure.

Please refer to FIG. 2, which is a flowchart of a method for presenting food information according to an embodiment of the disclosure. The method of the embodiment may be executed by the device for presenting food information 100 of FIG. 1, and the details of each step in FIG. 2 will be described below in conjunction with the elements shown in FIG. 1.

First, in Step S210, the processor 104 obtains a recommended calorie intake (hereinafter referred to as C) of a user (hereinafter referred to as A).

In an embodiment, the processor 104 may obtain physiological information of the user A, and determine an ideal weight of the user A accordingly. For example, assuming that the considered physiological information is the height of the user A, the processor 104 may, for example, determine the ideal weight of the user A according to the height of the user A and a predetermined indicator.

In an embodiment, the predetermined indicator is, for example, a certain specific body mass index (BMI) value. In different embodiments, the specific BMI value may be, for example, determined according to the gender, the age, or other characteristics of the user A. In an embodiment, a designer may, for example, select a moderate/ideal BMI value that may be used to characterize the weight of the human body as the specific BMI value, but not limited thereto.

In an embodiment, the processor 104 may, for example, determine the ideal weight of the user A based on the relationship of "ideal weight (kg)=height (m)$^2$×K", where K is the specific BMI value. In a first embodiment, assuming that the height of the user A is 165 cm and the specific BMI value (that is, K) is selected as 22, the ideal weight of the user A may be calculated as about 60 kg, but not limited thereto.

Afterwards, the processor 104 may determine the recommended calorie intake C of the user A based on the ideal weight of the user A. In an embodiment, the processor 104 may multiply the ideal weight of the user A by a scaling factor to obtain the recommended calorie intake C of the user A. In different embodiments, the recommended calorie intake C is, for example, the recommended calorie intake for a single day or the recommended calorie intake for a single meal, but not limited thereto.

In an embodiment where the recommended calorie intake C is the recommended calorie intake for a single day, the processor 104 may, for example, determine the scaling factor based on the daily activity level of the user A. For use 25 kcal as the scaling factor. In this case, the processor 104 may, for example, multiply the ideal weight of the user A by the scaling factor to obtain the recommended calorie intake C of the user A. In the first embodiment, assuming that the ideal weight of the user A is 60 kg and the selected scaling factor is 25 kcal, the corresponding recommended calorie intake C is, for example, 1500 kcal, but not limited thereto.

In another embodiment, assuming that the daily activity level of the user A is a moderate/intense activity level, the processor 104 may select 30 kcal/35 kcal as the corresponding scaling factors, but not limited thereto.

In an embodiment where the recommended calorie intake C is the recommended calorie intake for a single meal, the processor 104 may, for example, first determine the recommended calorie intake for a single day based on the above teachings, and then multiply the recommended calorie intake for a single day by a certain weight to determine the recommended calorie intake for a single meal. For example, assuming that the weights (which may be understood as calorie distribution ratios) of breakfast, lunch, and dinner are respectively 0.2, 0.4, and 0.4, the processor 104 may obtain the recommended calorie intake for a single day (for example, 1500 kcal) of the user, and then respectively multiply the recommended calorie intake for a single day by 0.2, 0.4, and 0.4 to obtain the recommended calorie intake for a single meal respectively corresponding to breakfast, lunch, and dinner, but not limited thereto.

For the convenience of explanation, it is assumed that the recommended calorie intake C considered in the following is the recommended calorie intake for a single day, but the same is only used as an example and is not intended to limit possible implementations of the disclosure.

After determining the recommended calorie intake of the user A, the processor 104 executes Step S220 to determine a reference portion size of each of multiple food types based on the recommended calorie intake C.

In an embodiment, the processor 104 may obtain a lookup table, wherein the lookup table records multiple predetermined calories and multiple predetermined food portion sizes corresponding to the predetermined calories, and the predetermined food portion sizes respectively correspond to the food types. Afterwards, the processor 104 may find a specific predetermined calorie closest to the recommended calorie intake C among the predetermined calories, and determine the reference portion size of each food type according to the predetermined food portion sizes corresponding to the specific predetermined calorie.

In an embodiment, the content of the lookup table may be exemplified as Table 1 below and may be, for example, determined according to a specific dietary guidebook.

TABLE 1

|  | 1500 kcal | 1800 kcal | 2000 kcal | 2200 kcal | 2500 kcal |
|---|---|---|---|---|---|
| Whole grains (bowl) | 2.5 | 3 | 3 | 3.5 | 4 |
| Protein food (serving) | 4 | 5 | 6 | 6 | 7 |
| Dairy product (cup) | 1.5 | 1.5 | 1.5 | 1.5 | 1.5 |
| Vegetables (serving) | 3 | 3 | 4 | 4 | 5 |
| Fruits (serving) | 2 | 2 | 3 | 3.5 | 4 |
| Oil, nuts, and seeds (serving) | 4 | 5 | 6 | 6 | 7 | example, assuming that user A is an office worker, the daily activity level may be estimated to be a light activity level. Relevant studies have pointed out that for people with the light activity level, the recommended calorie intake per kilogram is 25 kcal. Based on this, the processor 104 may In Table 1, the considered predetermined calories include, for example, 1500 kcal, 1800 kcal, 2000 kcal, 2200 kcal, and 2500 kcal, but not limited thereto. In addition, in Table 1, the considered food types include, for example, "whole grains", "protein food", "dairy product", "vegetables", "fruits", "oil, nuts, and seeds", etc., but not limited thereto.

It can be seen from Table 1 that the predetermined food portion sizes corresponding to 1500 kcal include, for example, 2.5 bowls of whole grains, 4 servings of protein food, 1.5 cups of dairy products, 3 servings of vegetables, 2 servings of fruits, and 4 servings of oil, nuts, and seeds. In addition, the predetermined food portion sizes corresponding to 1800 kcal include, for example, 3 bowls of whole grains, 1 serving of protein food, 1.5 cups of dairy products, 3 servings of vegetables, 2 servings of fruits, and 5 servings of oil, nuts, and seeds. Multiple predetermined food portion sizes corresponding to each of other predetermined calories may be deduced according to the above teachings and will not be elaborated here.

After obtaining the lookup table such as Table 1, the processor 104 may, for example, find the one closest to the recommended calorie intake C among the predetermined calories of 1500 kcal, 1800 kcal, 2000 kcal, 2200 kcal, and 2500 kcal as the specific predetermined calorie.

In the first embodiment, since the recommended calorie intake C is assumed to be 1500 kcal, the processor 104 may, for example, take 1500 kcal as the specific predetermined calorie, and determine the reference portion size of each of the food types with the predetermined food portion sizes corresponding to 1500 kcal. In this case, the reference portion size of whole grains is, for example, 2.5 bowls, the reference portion size of protein food is, for example, 4 servings, the reference portion size of dairy products is, for example, 1.5 cups, and the reference portion size of vegetables is, for example, 3 servings, the reference portion size of fruits is, for example, 2 servings, and the reference portion size of oil, nuts, and seeds is, for example, 4 servings.

It can be seen from the above example that the reference portion sizes of the food types are expressed in the same or different units. For example, the unit of the reference portion size of whole grains is "bowl", the unit of the reference portion size of protein food is "serving", the unit of the reference portion size of dairy products is "cup", the unit of the reference portion size of vegetables is "serving", the unit of the reference portion size of fruits is "serving", and the unit of the reference portion size of oil, nuts, and seeds is "serving". However, even though the same unit is used for the reference portion sizes of different food types, it does not mean that the volumes of the food types may be calculated using the same manner.

For example, although the unit of the reference portion sizes of protein food and oil, nuts, and seeds are both "serving", the volume of 1 serving of protein food should generally be different from the volume of 1 serving of oil, nuts, and seeds. It can be seen that it may be difficult for the content of Table 1 to be used to directly determine the volume corresponding to the reference portion size of each food type.

Based on this, the disclosure may determine the volume corresponding to the reference portion size of each food type through Steps S230 and S240 below.

In Step S230, the processor 104 determines a relative portion size of the reference portion size of each food type relative to a reference object (hereinafter referred to as O). In an embodiment of the disclosure, the reference object O is, for example, at least one of a palm and a fist, but not limited thereto.

In an embodiment, there may be a corresponding proportional relationship between a unit portion size of each food type and the reference object O. For example, there may be a first proportional relationship between the unit portion size of a first food type among the food types and the reference object O, there may be a second proportional relationship between the unit portion size of a second food type among the food types and the reference object O, and the first proportional relationship may be different from the second proportional relationship.

In an embodiment, the proportional relationship between the unit portion size of each food type and the reference object O may be as shown in Table 2 below.

TABLE 2

| Food type | Proportional relationship |
| --- | --- |
| Fruits | 1 serving = ¾ bowls = 1 fist |
| Vegetables | 1 serving = 1 bowl = 1.25 fists |
| Whole grains | 1 bowl = 1.25 fists |
| Protein food | 1 serving = ½ palm |

In the scenario in Table 2, 1 serving of fruits may correspond to 1 fist, 1 serving of vegetables may correspond to 1.25 fists, 1 bowl of whole grains may correspond to 1.25 fists, and 1 serving of protein food may correspond to ½ palm. In other words, the proportional relationship between fruits and fists is 1:1, the proportional relationship between vegetables and fists is 1:1.25, the proportional relationship between whole grains and fists is 1:1.25, and the proportional relationship between protein food and palms is 1:0.5, but not limited thereto.

Based on this, in the first embodiment, when the processor 104 intends to determine the relative portion size of the reference portion size of fruits (for example, 2 servings corresponding to 1500 kcal in Table 1) relative to the reference object O, the processor 104 may determine the relative portion size of the reference portion size of fruits relative to the reference object O based on the reference portion size of fruits and the corresponding proportional relationship (that is, 1:1). Since 2 servings of fruits may be understood as corresponding to 2 (that is, 2*1) fists, the relative portion size of the reference portion size of fruits relative to the reference object O is, for example, 2 servings, but not limited thereto.

In addition, in the first embodiment, when the processor 104 intends to determine the relative portion size of the reference portion size of vegetables (for example, 3 servings corresponding to 1500 kcal in Table 1) relative to the reference object O, the processor 104 may determine the relative portion size of the reference portion size of vegetables relative to the reference object O based on the reference portion size of vegetables and the corresponding proportional relationship (that is, 1:1.25). Since 3 servings of vegetables may be understood as corresponding to 3.75 (that is, 3*1.25) fists, the relative portion size of the reference portion size of vegetables relative to the reference object O is, for example, 3.75 servings, but not limited thereto.

Similarly, in the first embodiment, when the processor 104 intends to determine the relative portion size of the reference portion size of whole grains (for example, 2.5 bowls corresponding to 1500 kcal in Table 1) relative to the reference object O, the processor 104 may determine the relative portion size of the reference portion size of whole grains relative to the reference object O based on the reference portion size of whole grains and the corresponding proportional relationship (that is, 1:1.25). Since 2.5 bowls of whole grains may be understood as corresponding to 3.13 (that is, 2.5*1.25) palms, the relative portion size of the reference portion size of whole grains relative to the reference object O is, for example, 3.13 servings, but not limited thereto.

Furthermore, in the first embodiment, when the processor 104 intends to determine the relative portion size of the reference portion size of protein food (for example, 4 servings corresponding to 1500 kcal in Table 1) relative to the reference object O, the processor 104 may determine the relative portion size of the reference portion size of protein food relative to the reference object O based on the reference portion size of protein food and the corresponding proportional relationship (that is, 1:0.5). Since 4 servings of protein food may be understood as corresponding to 2 (that is, 4*0.5) palms, the reference portion size of protein food relative to the reference object O is, for example, 2 servings, but not limited thereto.

Next, in Step S240, the processor 104 determines a food volume corresponding to the relative portion size of each food type according to an object volume of the reference object O.

Figure 3:
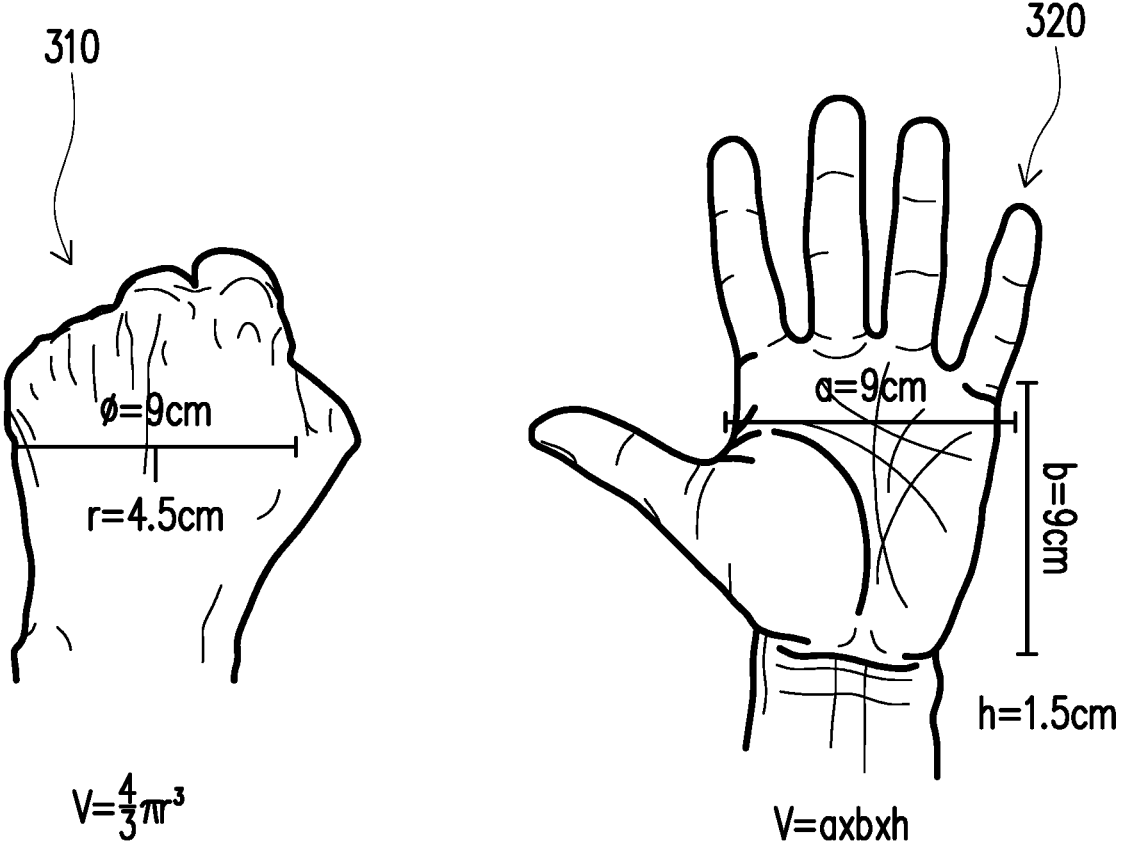
FIG. 3 is a schematic diagram of determining an object volume of a reference object according to an embodiment of the disclosure.

Please refer to FIG. 3, which is a schematic diagram of determining an object volume of a reference object according to an embodiment of the disclosure. In FIG. 3, it is assumed that the considered reference object O is a fist 310 with a width of 9 cm. In this case, if the fist 310 is regarded as a sphere with a radius (expressed as r) of 4.5 cm, the corresponding object volume may be estimated to be 382 cm³ based on the formula "$V=\frac{3}{4}\pi r^3$".

In addition, it is assumed that the considered reference object O is a palm 320 with a length and width of both 9 cm and a height of 1.5 cm. In this case, if the palm 320 is regarded as a cuboid with a length a, a width b, and a height h, the corresponding object volume may be estimated to be 122 cm³ based on the formula "$V=a \times b \times h$". Based on this, the content of Table 2 may be correspondingly updated to the content of Table 3 below.

TABLE 3

| Food type | Proportional relationship | Volume (cm³) |
|---|---|---|
| Fruits | 1 serving = ¾ bowls = 1 fist | 382 × 1 = 382 |
| Vegetables | 1 serving = 1 bowl = 1.25 fists | 382 × 1.25 = 478 |
| Whole grains | 1 bowl = 1.25 fists | 382 × 1.25 = 478 |
| Protein food | 1 serving = ½ palm | 122/2 = 61 |

It can be seen from Table 3 that the volume corresponding to 1 serving of fruits is, for example, 382 cm³, the volume Based on this, for one of the food types (hereinafter referred to as the first food type), the processor 104 may multiply the relative portion size corresponding to the first food type by the corresponding object volume as the food volume corresponding to the relative portion size of the first food type.

In the first embodiment, since the relative portion size of the reference portion size of fruits relative to the reference object O (for example, the fist) is assumed to be 2 servings, the processor 104 may determine that the food volume corresponding to the relative portion size of fruits is, for example, 764 cm³ (that is, 382×2). In the first embodiment, since the relative portion size of the reference portion size of vegetables relative to the reference object O (for example, the fist) is assumed to be 3.75 servings, the processor 104 may determine that the food volume corresponding to the relative portion size of vegetables is, for example, 1433 cm³ (that is, 382×3.75). In the first embodiment, since the relative portion size of the reference portion size of whole grains relative to the reference object O (for example, the fist) is assumed to be 3.13 servings, the processor 104 may determine that the food volume corresponding to the relative portion size of whole grains is, for example, 1196 cm³ (that is, 382×3.13). In the first embodiment, since the relative portion size of the reference portion size of protein food relative to the reference object O (for example, the palm) is assumed to be 2 servings, the processor 104 may determine that the food volume corresponding to the relative portion size of protein food is, for example, 244 cm³ (that is, 122×2), but not limited thereto.

In the embodiment of the disclosure, the food volume corresponding to each food type may be understood as the food volume that should be ingested corresponding to each food type, but not limited thereto.

Next, in Step S250, the processor 104 generates a pie chart according to the food volume corresponding to each food type.

In an embodiment, during the process of executing Step S250, the processor 104 may obtain the volume sum of the food volumes corresponding to the food types, and determine the volume ratio of the food volume corresponding to each food type in the volume sum.

In the first embodiment, the volume sum of the food volumes corresponding to the food types is, for example, 3637 cm³, and the volume ratio corresponding to each food type may be exemplified in Table 4 below.

TABLE 4

| Food type | Reference portion size | Relative portion size | Food volume (that should be ingested) (cm³) | Volume ratio |
|---|---|---|---|---|
| Fruits | 2 servings | 2 servings (that is, 2 fists) | 764 | 21% |
| Vegetables | 3 servings | 3.75 servings (that is, 3.75 fists) | 1,433 | 39% |
| Whole grains | 2.5 bowls | 3.13 servings (that is, 3.13 fists) | 1,196 | 33% |
| Protein food | 4 servings | 2 servings (that is, 2 palms) | 244 | 7% |
| Total | | | 3637 | 100% | corresponding to 1 serving of vegetables is, for example, 478 cm³, the volume corresponding to 1 bowl of whole grains is, for example, 478 cm³, and the volume corresponding to 1 serving of protein food is, for example, 61 cm³, but not limited thereto.

In the embodiment of the disclosure, Table 4 may be understood as being generated based on the relevant content corresponding to 1500 kcal in Table 1. Therefore, based on the above teachings, the processor 104 may correspondingly determine the volume ratio of each food type corresponding to other predetermined calories, and the relevant content may be as shown in Table 5 below.

TABLE 5

| Food type | 1200 kcal | 1500 kcal | 1800 kcal | 2000 kcal | 2200 kcal | 2500 kcal |
|---|---|---|---|---|---|---|
| Fruits | 25% | 21% | 19% | 24% | 25% | 24% |
| Vegetables | 46% | 39% | 36% | 39% | 36% | 38% |
| Whole grains | 23% | 33% | 36% | 30% | 32% | 31% |
| Protein food | 6% | 7% | 8% | 8% | 7% | 7% |

After determining the volume ratio corresponding to each food type, the processor 104 may determine a central angle corresponding to each food type according to the volume ratio corresponding to each food type, and draw the pie chart accordingly.

For ease of understanding, the first embodiment is still used as an illustrative example below, but not limited thereto.

In the first embodiment, the processor 104 may multiply 360 degrees by the volume ratio corresponding to each food type to determine the central angle corresponding to each food type, as shown in Table 6 below.

TABLE 6

| Order | Food type | Volume ratio | Central angle |
|---|---|---|---|
| 1 | Fruits | 21% | 76° (that is, 360° × 21%) |
| 2 | Vegetables | 39% | 142° (that is, 360° × 39%) |
| 3 | Whole grains | 33% | 118° (that is, 360° × 33%) |
| 4 | Protein food | 7% | 24° (that is, 360° × 7%) |

In an embodiment of the disclosure, the pie chart may include multiple specific sectors corresponding to the food types, and the central angle corresponding to each specific sector is positively correlated with the corresponding food volume.

Based on this, after determining the central angle corresponding to each food type, the processor 104 may draw the pie chart accordingly.

In an embodiment, the processor 104 may first sort the food types according to Table 6. Next, for the i-th food type among the food types, the processor 104 may obtain a reference angle, and draw a sector from the reference angle, wherein the central angle of the sector corresponds to the central angle of the i-th food type, the sector has a first side and a second side with a length of a predetermined radius, and the first side of the sector corresponds to the reference angle, wherein 1≤i≤N, where N is the number of the food types.

In an embodiment, when i is 1, the reference angle is 0 degrees. In other embodiments, when i is greater than 1, the processor 104 may obtain a reference sector corresponding to the (i-1)-th food type among the food types, wherein the reference sector has a first reference side and a second reference side. Afterwards, the processor 104 may use an angle corresponding to the second reference side as the reference angle.

Figure 4:
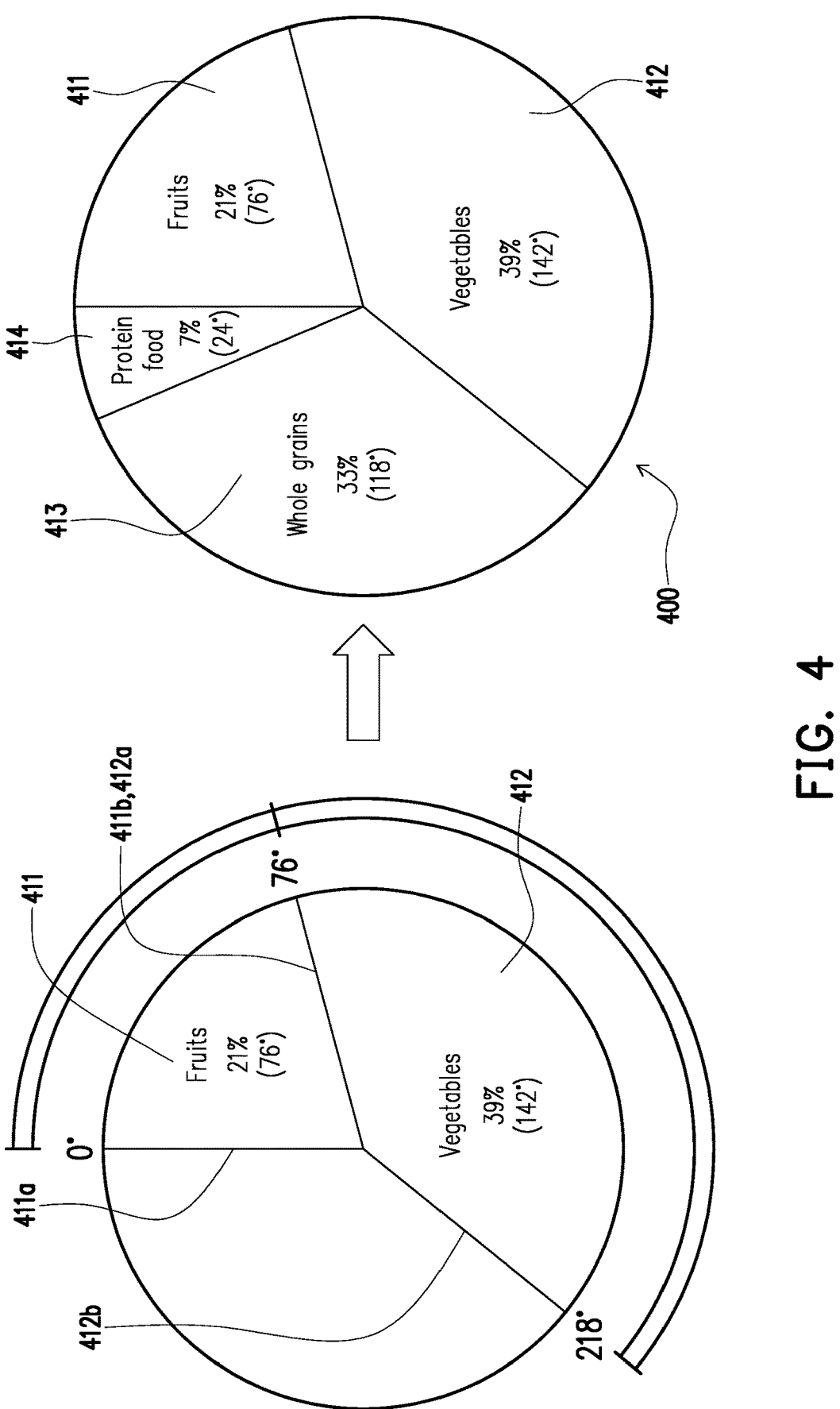
FIG. 4 is a schematic diagram of drawing a pie chart according to a first embodiment of the disclosure.

Please refer to FIG. 4, which is a schematic diagram of drawing a pie chart according to a first embodiment of the disclosure. In FIG. 4, the processor 104 may sequentially draw the sectors of the 4 food types in Table 6.

Specifically, for fruits (that is, the first food type), the processor 104 may use 0 degrees as the reference angle, and draw a sector 411 with a central angle of 76 degrees from 0 degrees. It can be seen from FIG. 4 that the sector 411 has a predetermined radius R, a first side 411a (corresponding to 0 degrees) and a second side 411b.

Next, for vegetables (that is, the second food type), the processor 104 may first obtain the sector 411 of fruits (that is, the first food type) as the reference sector, and respectively regard the first side 411a and the second side 411b as the first reference side and the second reference side. In this case, the processor 104 may use an angle (that is, 76 degrees) corresponding to the second reference side (that is, the second side 411b) as the reference angle.

In this case, the processor 104 may draw a sector 412 with a central angle of 142 degrees from 76 degrees. It can be seen from FIG. 4 that the sector 412 has the predetermined radius R, a first side 412a (corresponding to 76 degrees), and a second side 412b (corresponding to 218 degrees).

Based on the above principles, the processor 104 may correspondingly draw a sector 413 (with a central angle of 118 degrees) corresponding to whole grains and a sector 414 (with a central angle of 24 degrees) corresponding to protein food, thereby completing a pie chart 400.

It can be seen from FIG. 4 that the sectors 411 to 414 respectively occupy 21%, 39%, 33%, and 7% of the pie chart 400, which respectively correspond to the volume ratios of the food types in Table 6.

Figure 5:
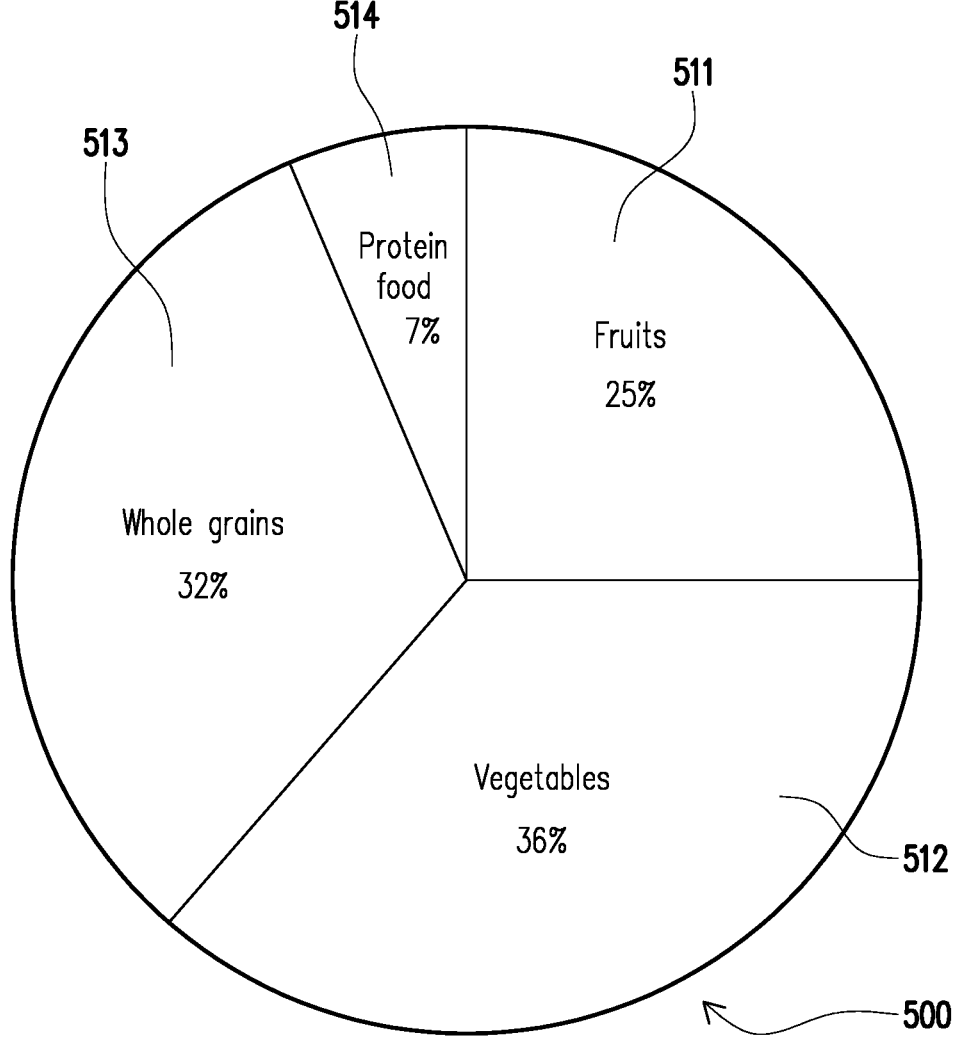
FIG. 5 is a schematic diagram of drawing a pie chart according to another embodiment of the disclosure.

Please refer to FIG. 5, which is a schematic diagram of drawing a pie chart according to another embodiment of the disclosure. In FIG. 5, the processor 104 may draw a pie chart 500 according to the content corresponding to 2200 kcal in Table 5. In the embodiment, the pie chart 500 may include sectors 511 to 514 respectively corresponding to fruits, vegetables, whole grains, and protein food, and reference may be made to the relevant description of FIG. 4 for the relevant drawing principles, which will not be elaborated here.

It can be seen from the above that a method according to an embodiment of the disclosure may provide the user A with a personalized recommended dietary intake in the form of a pie chart after determining the recommended calorie intake of the user A according to the physiological information of the user A. Moreover, since the method of the disclosure involves determining the food volume corresponding to each food type based on the object volume of the reference object, and determining the corresponding sector in the pie chart accordingly, the method allows the user A to understand the intake of each food type more clearly and may also make it easier for the user A to record his own dietary condition. In other embodiments, the user A may adjust the intake of each food type in the three meals according to his own dietary habits, and the processor 104 may generate a reference pie chart corresponding to the three meals accordingly. Based on this, when the user A uses a circular plate, the intake of each food type in the circular plate may be arranged in response to the pie chart.

In some embodiments, the method according to the embodiment of the disclosure may also update the pie chart according to the intake condition of each food type by the user A.

Figure 6:
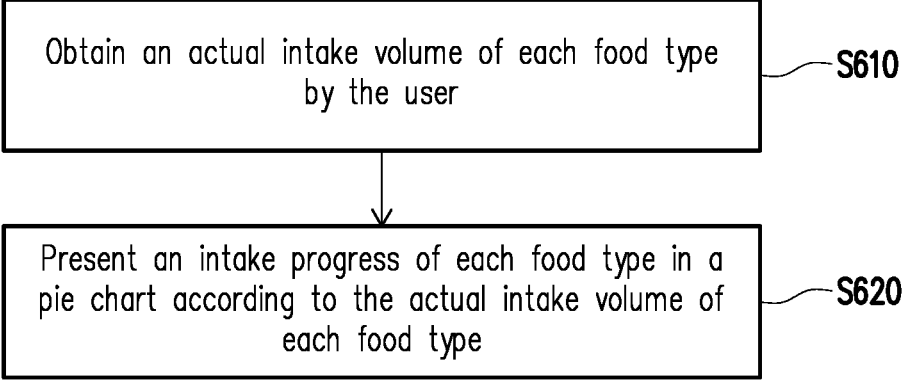
FIG. 6 is a flowchart of updating a pie chart according to an embodiment of the disclosure.

Please refer to FIG. 6, which is a flowchart of updating a pie chart according to an embodiment of the disclosure. First, in Step S610, the processor 104 may obtain an actual intake volume of each food type by the user A, and present an intake progress of each food type in the pie chart according to the actual intake volume of each food type in Step S620.

Figure 7:
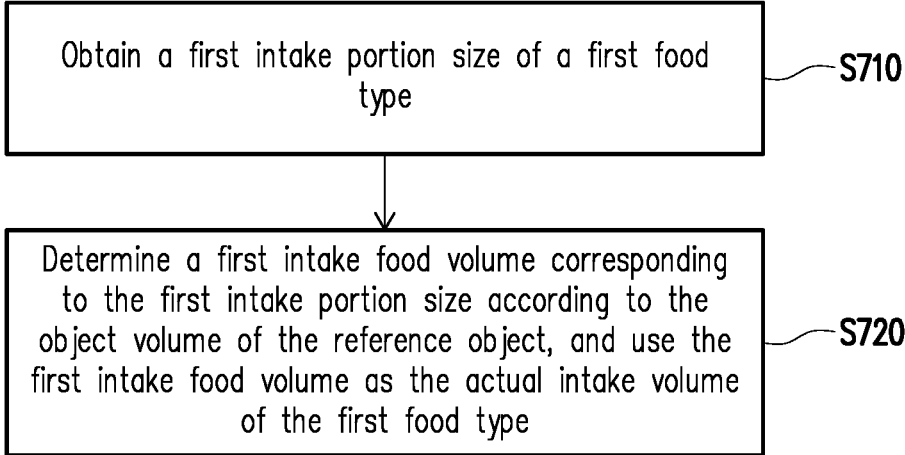
FIG. 7 is a flowchart of determining a first intake portion size of a first food type according to FIG. 6.

In an embodiment, the processor 104 may implement Step S610 through executing the process of FIG. 7. Please refer to FIG. 7, which is a flowchart of determining a first intake portion size of a first food type according to FIG. 6.

First, in Step S710, the processor 104 may obtain the first intake portion size of the first food type. In different embodiments, the processor 104 may obtain the first intake portion size of the first food type through different manners.

In an embodiment, the method of the disclosure may be implemented as a specific application program installed on the device for presenting food information 100, and the specific application program may provide a relevant input interface for the user A to input the corresponding intake portion size for one or more food types.

In an embodiment, the user A may, for example, input the corresponding intake portion size for each food type in the input interface. In the first embodiment, assuming that the user A ingests 0 servings of fruits, 1.5 servings of vegetables, 2 bowls of whole grains, and 4 servings of protein food, the user A may input in the input interface accordingly, but not limited thereto. In another embodiment, the user A may input the intake portion size of each food type, such as one fist of fruits, one fist of vegetables, and one palm of protein food, in the input interface.

In another embodiment, the user A may also input the intake portion size corresponding to a certain food type by providing an image to the device for presenting food information 100 through a lens.

In the first embodiment, when the user A intends to input the intake portion size corresponding to protein food, the user A may place his palm as the reference object O next to the food to be ingested (for example, sliced meat, hereinafter referred to as first food), and correspondingly capture a first image including the palm and the first food. In this case, the processor 104 may obtain the first image, and find an object image region corresponding to the reference object O (for example, the palm) and a food image region corresponding to the first food in the first image through a pre-trained artificial intelligence model (or other similar image processing functions). Afterwards, the processor 104 may determine the intake portion size of protein food based on a ratio between the object image region and the food image region. In the first embodiment, assuming that the ratio of the food image region to the object image region is 2:1, the first intake portion size of the first food type may be, for example, estimated to be 4 servings (that is, 2 palms) according to content of Table 3.

vegetable based on a ratio between the object image region and the food image region. For example, if the ratio of the food image region to the object image region is 1.5:1, the intake portion size of a first food type may be, for example, estimated to be 1.5 servings (that is, 1.5 fists) according to the content of Table 3.

In other embodiments, after obtaining the first image, the processor 104 may directly identify the first food type corresponding to the first food and/or the shape of the reference object O (for example, the palm or the fist) with the artificial intelligence model, and subsequently determine the first intake portion size of the first food type according to the above teachings, but not limited thereto.

After obtaining the first intake portion size of the first food type, the processor 104 may determine a first intake food volume corresponding to the first intake portion size according to the object volume of the reference object O, and use the first intake food volume as the actual intake volume of the first food type in Step S720.

In the first embodiment, since the intake portion size of protein food is assumed to be 4 servings, the intake food volume of protein food may be determined as 244 cm$^3$ (that is, 61×4) according to Table 3, and the processor 104 may use 244 cm$^3$ as the actual intake volume of protein food. In addition, in the first embodiment, since the intake portion size corresponding to vegetables is assumed to be 1.5 servings, the intake food volume of vegetables may be determined as 717 cm$^3$ (that is, 478×1.5) according to Table 3, and the processor 104 may use 717 cm$^3$ as the actual intake volume of vegetables.

In the first embodiment, the processor 104 may correspondingly determine that the actual intake volume of fruits is, for example, 0 cm$^3$ and the actual intake volume of whole grains is, for example, 955 cm$^3$ based on the above teachings.

Please refer to FIG. 6 again. After obtaining the actual intake volume of each food type, the processor 104 may execute Step S620 to present the intake progress of each food type in the pie chart 400 according to the actual intake volume of each food type.

In the first embodiment, the actual intake volume corresponding to each food type may be organized into Table 7 below together with the food volume (that should be ingested) of Table 4.

TABLE 7

| Food type | Actual intake volume (cm$^3$) | Food volume (that should be ingested) (cm$^3$) | Actual intake ratio |
|---|---|---|---|
| Fruits | 0 | 764 | 0% |
| Vegetables | 714 | 1,433 | 50% |
| Whole grains | 955 | 1,196 | 80% |
| Protein food | 244 | 244 | 100% |

In a second embodiment, when the user A intends to input the intake portion size of a corresponding vegetable, the user A may place his fist as the reference object O next to first food to be ingested (for example, a certain vegetable), and correspondingly captures a first image including the fist and the first food. In this case, the processor 104 may obtain the first image, and find an object image region corresponding to the reference object O (for example, the fist) and a food image region corresponding to the first food in the first image through a pre-trained artificial intelligence model (or other similar image processing functions). Afterwards, the processor 104 may determine the intake portion size of the It can be seen from Table 7 that in the first embodiment, the actual intake ratio of fruits is 0% (that is, 0/764), the actual intake ratio of vegetables is 50% (that is, 714/1433), the actual intake ratio of whole grains is 80% (that is, 955/1196), and the actual intake ratio of protein food is 100% (that is, 244/244). Based on this, the processor 104 may correspondingly update the pie chart 400, as shown in FIG. 8.

Figure 8:
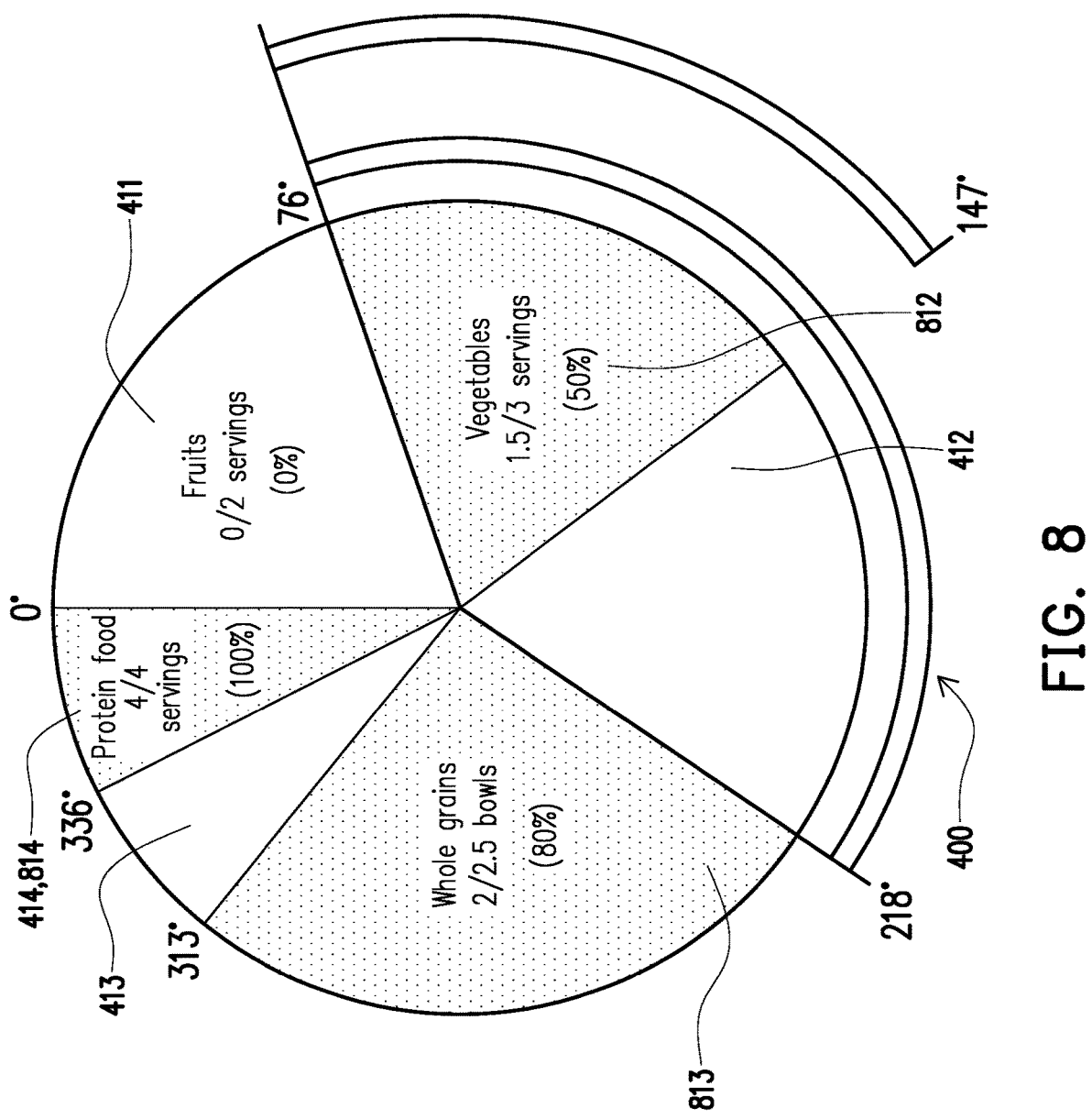
FIG. 8 is a schematic diagram of updating a pie chart according to FIG. 4.

Please refer to FIG. 8, which is a schematic diagram of updating a pie chart according to FIG. 4. In FIG. 8, since the actual intake ratio of fruits is 0%, the processor 104 may not mark any sector 411 corresponding to fruits. Since the actual intake ratio of vegetables is 50%, the processor 104 may first take 50% of the central angle (that is, 142 degrees) of the sector 412 corresponding to vegetables as a specific angle (that is, 71 degrees), and then draw a sector 812 (which may have a color different from that of the sector 412) with a central angle of 71 degrees (that is, the specific angle) from the reference angle (that is, 76 degrees) corresponding to the sector 412. In this way, the intake progress of vegetables may be presented.

In addition, since the actual intake ratio of whole grains is 80%, the processor 104 may first take 80% of the central angle (that is, 118 degrees) of the sector 413 corresponding to whole grains as a specific angle (that is, 95 degrees), and then draw a sector 813 (which may have a color different from that of the sector 413) with a central angle of 95 degrees (that is, the specific angle) from the reference angle (that is, 218 degrees) corresponding to the sector 413. In this way, the intake progress of whole grains may be presented.

Since the actual intake ratio of protein food is 100%, the processor 104 may first take 100% of the central angle (that is, 24 degrees) of the sector 414 corresponding to protein food as a specific angle (that is, 24 degrees), and then draw a sector 814 (which may have a color different from that of the sector 414) with a central angle of 24 degrees (that is, the specific angle) from the reference angle (that is, 336 degrees) corresponding to the sector 414. In this way, the intake progress of protein food may be presented.

The disclosure further provides a computer readable storage medium for executing the method for presenting food information. The computer readable storage medium is composed of multiple program commands (for example, a setting program command and a deployment program command) contained therein. The program commands may be loaded into the device for presenting food information 100 and executed by the device for presenting food information 100 to execute the method for presenting food information and the functions of the device for presenting food information 100.

In summary, the method according to the embodiment of the disclosure may provide the user with the personalized recommended dietary intake in the form of the pie chart after determining the recommended calorie intake of the user according to the physiological information of the user. Moreover, since the method of the disclosure involves determining the food volume corresponding to each food type based on the object volume of the reference object, and determining the corresponding sector in the pie chart accordingly, the method allows the user to understand the intake of each food type more clearly.

In addition, the disclosure may also present the corresponding intake progress in the pie chart according to the actual intake volume of each food type by the user, thereby allowing the user to grasp his own dietary condition more clearly.

Although the disclosure has been disclosed in the above embodiments, the embodiments are not intended to limit the disclosure. Persons skilled in the art may make some changes and modifications without departing from the spirit and scope of the disclosure. Therefore, the protection scope of the disclosure shall be defined by the appended claims.

What is claimed is:

1. A method for presenting food information, suitable for a device for presenting food information, comprising:
    obtaining, by a processor, a recommended calorie intake of a user;

determining, by the processor, a reference portion size of each of a plurality of food types based on the recommended calorie intake;
    determining, by the processor, a relative portion size of the reference portion size of each of the food types relative to a reference object, wherein the reference object comprises at least one of a palm and a first of the user;
    determining, by the processor, a food volume corresponding to the relative portion size of each of the food types according to an object volume of the reference object, wherein the object volume is calculated based on a three-dimensional geometric model corresponding to said at least one of the palm and the first of the user;
    generating, by the processor, a pie chart according to the food volume corresponding to each of the food types;
    storing, by the processor, the pie chart in a memory; and
    outputting, by the processor, the pie chart in a monitor,
    wherein the food types comprise a first food type, there is a first proportional relationship between a unit portion size of the first food type and the reference object, and the step of determining the relative portion size of the reference portion size of each of the food types relative to the reference object comprises:
    determining the relative portion size of the reference portion size of the first food type relative to the reference object based on the reference portion size of the first food type and the first proportional relationship,
    wherein the step of generating the pie chart comprises:
    obtaining a volume sum of the food volumes corresponding to the plurality of food types;
    determining a volume ratio of the food volume corresponding to each of the food types in the volume sum; and
    determining a central angle for a sector in the pie chart corresponding to each of the food types according to the volume ratio corresponding to each of the food types,
    wherein in a case that the reference object is the fist, the three-dimensional geometric model is a sphere model, and in a case that the reference object is the palm, the three-dimensional geometric model is a cuboid model.

2. The method according to claim 1, wherein the step of obtaining the recommended calorie intake of the user comprises:
    obtaining physiological information of the user, and determining an ideal weight of the user; and
    determining the recommended calorie intake of the user based on the ideal weight of the user.

3. The method according to claim 1, wherein the step of determining the reference portion size of each of the food types based on the recommended calorie intake comprises:
    obtaining a lookup table, wherein the lookup table records a plurality of predetermined calories and a plurality of predetermined food portion sizes corresponding to each of the predetermined calories, and the predetermined food portion sizes respectively correspond to the food types;
    finding a specific predetermined calorie closest to the recommended calorie intake among the predetermined calories, and determining the reference portion size of each of the food types according to the predetermined food portion sizes corresponding to the specific predetermined calorie.

4. The method according to claim 1, the food types further comprise a second food type, there is a second proportional relationship between a unit portion size of the second food type and the reference object, and the step of determining the relative portion size of the reference portion size of each of the food types relative to the reference object further comprises: determining the relative portion size of the reference portion size of the second food type relative to the reference object based on the reference portion size of the second food type and the second proportional relationship, wherein the first proportional relationship is different from the second proportional relationship.

5. The method according to claim 1, wherein the food types comprise a first food type, and the step of determining the food volume corresponding to the relative portion size of each of the food types according to the object volume of the reference object comprises:

multiplying the relative portion size corresponding to the first food type by the object volume as the food volume corresponding to the relative portion size of the first food type.

6. The method according to claim 1, wherein the pie chart comprises a plurality of specific sectors corresponding to the food types, and a central angle corresponding to each of the specific sectors is positively correlated with the corresponding food volume.

7. The method according to claim 6, wherein the step of generating the pie chart according to the food volume corresponding to each of the food types comprises:

obtaining a volume sum of the food volumes corresponding to the food types, and determining a volume ratio of the food volume corresponding to each of the food types in the volume sum;

determining the central angle corresponding to each of the food types according to the volume ratio corresponding to each of the food types, and drawing the pie chart.

8. The method according to claim 7, wherein the step of drawing the pie chart comprises:

obtaining a reference angle for an i-th food type among the food types, and drawing a sector from the reference angle, wherein a central angle of the sector corresponds to the central angle of the i-th food type, the sector has a first side and a second side with a length of a predetermined radius, and the first side of the sector corresponds to the reference angle, wherein, where N is a number of the food types.

9. The method according to claim 8, wherein in response to i being 1, the reference angle is 0 degrees, and in response to i being greater than 1, the step of obtaining the reference angle comprises:

obtaining a reference sector corresponding to an (i-1)-th food type among the food types, wherein the reference sector has a first reference side and a second reference side;

using an angle corresponding to the second reference side as the reference angle.

10. The method according to claim 1, wherein the recommended calorie intake comprises a recommended calorie intake for a single day or a recommended calorie intake for a single meal.

11. The method according to claim 1, further comprising:

obtaining an actual intake volume of each of the food types by the user; and presenting an intake progress of each of the food types in the pie chart according to the actual intake volume of each of the food types.

12. The method according to claim 11, wherein the food types comprise a first food type, and the step of obtaining the actual intake volume of each of the food types by the user comprises:

obtaining a first intake portion size of the first food type;

determining a first intake food volume corresponding to the first intake portion size according to the object volume of the reference object, and using the first intake food volume as the actual intake volume of the first food type.

13. The method according to claim 12, wherein the step of obtaining the first intake portion size of the first food type comprises:

obtaining a first image, wherein the first image comprises an object image region corresponding to the reference object and a food image region corresponding to first food, and the first food belongs to the first food type;

determining the first intake portion size of the first food type based on a ratio between the object image region and the food image region.

14. The method according to claim 11, wherein the food types comprise a first food type, the pie chart comprises a first sector corresponding to the first food type, the first sector has a reference angle and a first central angle, and the intake progress of the first food type is characterized as a second sector, wherein the second sector starts from the reference angle and has a second central angle, and a ratio between the second central angle and the first central angle corresponds to an actual intake ratio of the first food type by the user.

15. The method according to claim 1, further comprising:

obtaining an intake of each of the food types in three meals set by the user, and generating a plurality of reference pie charts corresponding to the three meals.

16. A device for presenting food information, comprising:

a storage circuit, storing a program code; and a processor, coupled to the storage circuit and accessing the program code to execute:

obtaining a recommended calorie intake of a user;

determining a reference portion size of each of a plurality of food types based on the recommended calorie intake;

determining a relative portion size of the reference portion size of each of the food types relative to a reference object, wherein the reference object comprises at least one of a palm and a first of the user;

determining a food volume corresponding to the relative portion size of each of the food types according to an object volume of the reference object, wherein the object volume is calculated based on a three-dimensional geometric model corresponding to said at least one of the palm and the first of the user;

generating a pie chart according to the food volume corresponding to each of the food types;

storing, by the processor, the pie chart in a memory; and outputting, by the processor, the pie chart in a monitor, wherein the food types comprise a first food type, there is a first proportional relationship between a unit portion size of the first food type and the reference object, and the step of determining the relative portion size of the reference portion size of each of the food types relative to the reference object comprises:

determining the relative portion size of the reference portion size of the first food type relative to the reference object based on the reference portion size of the first food type and the first proportional relationship, wherein the step of generating the pie chart comprises:

obtaining a volume sum of the food volumes corresponding to the plurality of food types;

determining a volume ratio of the food volume corresponding to each of the food types in the volume sum; and determining a central angle for a sector in the pie chart corresponding to each of the food types according to the volume ratio corresponding to each of the food types, wherein in a case that the reference object is the fist, the three-dimensional geometric model is a sphere model, and in a case that the reference object is the palm, the three-dimensional geometric model is a cuboid model.

17. The device for presenting food information according to claim 16, wherein the processor further executes:

obtaining an actual intake volume of each of the food types by the user; and presenting an intake progress of each of the food types in the pie chart according to the actual intake volume of each of the food types.

18. A computer readable storage medium, wherein the computer readable storage medium records an executable computer program, and the executable computer program is loaded by a device for presenting food information to execute:

obtaining a recommended calorie intake of a user;

determining a reference portion size of each of a plurality of food types based on the recommended calorie intake;

determining a relative portion size of the reference portion size of each of the food types relative to a reference object, wherein the reference object comprises at least one of a palm and a first of the user;

determining a food volume corresponding to the relative portion size of each of the food types according to an object volume of the reference object, wherein the object volume is calculated based on a three-dimensional geometric model corresponding to said at least one of the palm and the first of the user;

generating a pie chart according to the food volume corresponding to each of the food types;

storing the pie chart in a memory; and outputting the pie chart in a monitor, wherein the food types comprise a first food type, there is a first proportional relationship between a unit portion size of the first food type and the reference object, and the step of determining the relative portion size of the reference portion size of each of the food types relative to the reference object comprises:

determining the relative portion size of the reference portion size of the first food type relative to the reference object based on the reference portion size of the first food type and the first proportional relationship, wherein the step of generating the pie chart comprises:

obtaining a volume sum of the food volumes corresponding to the plurality of food types;

determining a volume ratio of the food volume corresponding to each of the food types in the volume sum; and determining a central angle for a sector in the pie chart corresponding to each of the food types according to the volume ratio corresponding to each of the food types, wherein in a case that the reference object is the fist, the three-dimensional geometric model is a sphere model, and in a case that the reference object is the palm, the three-dimensional geometric model is a cuboid model.

* * * * *